US008262876B2

(12) United States Patent
Manabe et al.

(10) Patent No.: US 8,262,876 B2
(45) Date of Patent: Sep. 11, 2012

(54) TEST PIECE FOR MEASURING BIOLOGICAL SAMPLE AND BIOLOGICAL SAMPLE MEASUREMENT APPARATUS

(75) Inventors: Kazuo Manabe, Ehime (JP); Norio Imai, Ehime (JP); Akiyoshi Oozawa, Ehime (JP)

(73) Assignee: Panasonic Corporation, Osaka (JP)

( * ) Notice: Subject to any disclaimer, the term of this patent is extended or adjusted under 35 U.S.C. 154(b) by 464 days.

(21) Appl. No.: 12/528,725

(22) PCT Filed: Dec. 8, 2008

(86) PCT No.: PCT/JP2008/003655
§ 371 (c)(1),
(2), (4) Date: Aug. 26, 2009

(87) PCT Pub. No.: WO2009/075093
PCT Pub. Date: Jun. 18, 2009

(65) Prior Publication Data
US 2010/0108508 A1    May 6, 2010

(30) Foreign Application Priority Data

Dec. 12, 2007  (JP) ................................. 2007-320378
Dec. 21, 2007  (JP) ................................. 2007-329722

(51) Int. Cl.
*G01N 27/327*    (2006.01)
*G01N 27/416*    (2006.01)
(52) U.S. Cl. ................. 204/406; 204/403.01; 422/82.01
(58) Field of Classification Search ........ 204/403.01–403.15, 406, 271; 422/82.01; 435/4, 10–28
See application file for complete search history.

(56) References Cited

U.S. PATENT DOCUMENTS

| 6,560,471 | B1 | 5/2003 | Heller et al. |
| 2003/0100821 | A1 | 5/2003 | Heller et al. |
| 2003/0159945 | A1* | 8/2003 | Miyazaki et al. .......... 205/777.5 |
| 2003/0178302 | A1* | 9/2003 | Bhullar et al. ........... 204/403.01 |
| 2005/0023137 | A1 | 2/2005 | Bhullar et al. |
| 2005/0023152 | A1 | 2/2005 | Surridge et al. |
| 2006/0226985 | A1 | 10/2006 | Goodnow et al. |
| 2007/0237678 | A1 | 10/2007 | Roesicke et al. |

(Continued)

FOREIGN PATENT DOCUMENTS

JP    2002-251461    9/2002

(Continued)

OTHER PUBLICATIONS

Supplementary European Search Report issued Jul. 22, 2011 in European Application No. EP 08 86 0328.

(Continued)

*Primary Examiner* — J. Christopher Ball
(74) *Attorney, Agent, or Firm* — Wenderoth, Lind & Ponack, L.L.P.

(57) ABSTRACT

A blood glucose measurement device (50) comprises a test piece insertion unit (10) for inserting, holding, and electrically connecting a test piece on which an electrode pattern has been formed, a measurement circuit (16) for electrochemically measuring a biological sample that has been placed in the form of a spot on the test piece, a communication circuit (15) for transmitting the result of measurement with the measurement circuit (16) by wireless communication using an antenna electrode (2C) equipped with the test piece, and a switch (14) that is connected to the test piece insertion unit (10) for switching between the measurement circuit (16) and the communication circuit (15).

16 Claims, 13 Drawing Sheets

U.S. PATENT DOCUMENTS

| | | |
|---|---|---|
| 2007/0270672 A1 | 11/2007 | Hayter |
| 2008/0114228 A1 | 5/2008 | McCluskey et al. |
| 2010/0063374 A1 | 3/2010 | Goodnow et al. |
| 2010/0089750 A1 | 4/2010 | Goodnow et al. |
| 2010/0148972 A1 | 6/2010 | Goodnow et al. |
| 2010/0152561 A1 | 6/2010 | Goodnow et al. |
| 2010/0152562 A1 | 6/2010 | Goodnow et al. |

FOREIGN PATENT DOCUMENTS

| | | |
|---|---|---|
| JP | 2004-520898 | 7/2004 |
| JP | 2007-33459 | 2/2007 |
| WO | 02/058537 | 8/2002 |
| WO | 2004/113910 | 12/2004 |
| WO | 2006/026748 | 3/2006 |
| WO | 2006/040083 | 4/2006 |
| WO | 2006/086423 | 8/2006 |

OTHER PUBLICATIONS

International Search Report issued Mar. 10, 2009 in International (PCT) Application No. PCT/JP2008/003655, filed Dec. 8, 2008.

* cited by examiner

TEST PIECE FOR MEASURING BIOLOGICAL SAMPLE AND BIOLOGICAL SAMPLE MEASUREMENT APPARATUS

TECHNICAL FIELD

The present invention relates to a test piece for measuring a biological sample and to a biological sample measurement apparatus, and more particularly relates to a technology for the wireless communication of measurement data from a biological sample measurement apparatus.

BACKGROUND ART

Recent years have witnessed the use of data transmission apparatus equipped with a measurement apparatus such as a blood glucose meter or a blood pressure meter (biological sample measurement apparatus) and a portable terminal apparatus for acquiring the measurement information by wireless communication (see, for example, Patent Document 1). In Patent Document 1, the measurement data measured by the measurement apparatus is sent by the portable terminal apparatus via a network to a data processor installed in a medical facility or the like.
Patent Document 1: Japanese Laid-Open Patent Application 2002-251461 (disclosed on Sep. 6, 2002).

SUMMARY

However, with the apparatus disclosed in the above-mentioned publication, if the biological sample measurement apparatus is so small that it is covered by the hand in which it is held, a problem is that the transmission power has to be increased to prevent a decrease in transmission performance when the radio waves emitted from the antenna provided inside the biological sample measurement apparatus are absorbed by the hand that holds the apparatus. It is an object of the present invention to reduce the effect of the absorption of radio waves by the user's hand, even with a small biological sample measurement apparatus, and thereby allow the radio waves to be emitted more efficiently and the transmission power to be kept low.

TECHNICAL SOLUTION

To achieve the stated object, the test piece for measuring a biological sample according to the first invention is one in which the test piece is inserted and held with a biological sample deposited in a biological sample measurement apparatus, and is electrically connected to the biological sample measurement apparatus, this test piece comprising a measurement electrode and an antenna electrode. The measurement electrode is for electrochemically measuring the biological sample that has been placed in the form of a spot in a specific location. The antenna electrode functions as a communications antenna in a state of being inserted and held in the biological sample measurement apparatus.

Here, for example, a measurement-use electrode pattern (measurement electrode) and a communication-use electrode pattern (antenna electrode) are provided on one side of a test piece mounted in a biological sample measurement apparatus capable of transmitting to a medical facility server, data processor, or the like.

The above-mentioned electrode patterns that function as a measurement electrode and an antenna electrode may be provided individually, or may be provided as a single electrode pattern.

Consequently, even if the test piece is mounted in a compact biological sample measurement apparatus, the communication-use radio waves will not be absorbed by the hand in which the apparatus is held. As a result, the radio waves will be emitted from the test piece side more efficiently, and the transmission power can be kept low.

The test piece for measuring a biological sample according to the second invention is the test piece for measuring a biological sample according to the first invention, wherein the measurement electrode also serves as the antenna electrode.

The measurement electrode and antenna electrode required on the test piece side here are both constituted by a single electrode pattern.

Consequently, measurement of the biological sample and communication can both be accomplished by forming just one electrode pattern within the test piece. Thus, the size of the test piece and the apparatus can be reduced.

A biological sample measurement apparatus according to the third invention comprises the test piece for measuring a biological sample according to the first or second invention, a test piece insertion unit, a measurement circuit, and a communication circuit. The test piece insertion unit is used for inserting, holding, and electrically connecting the test piece. The measurement circuit electrochemically measures a biological sample that has been placed in the form of a spot on the test piece. The communication circuit transmits the result measured with this measurement circuit by wireless communication.

The biological sample measurement apparatus according to the fourth invention is the biological sample measurement apparatus according to the third invention, further comprising a switch that is connected to the test piece insertion unit, for switching between the measurement circuit and the communication circuit.

The biological sample measurement apparatus according to the fifth invention is the biological sample measurement apparatus according to the third invention, further comprising an antenna pattern disposed between the communication circuit and an electrode within the test piece insertion unit to which the antenna electrode of the test piece is connected.

Here, when a test piece is mounted, an antenna pattern connected to an antenna electrode provided on the test piece side is provided on the apparatus side.

Consequently, when a test piece is inserted into the test piece insertion unit, the antenna electrode on the test piece side and the antenna pattern can function as an integrated antenna. Thus, the electrode pattern functioning as an antenna can be made larger, which further enhances communication performance.

The biological sample measurement apparatus according to the sixth invention is the biological sample measurement apparatus according to any one of the third to fifth inventions, further comprising an insertion/removal detection circuit for detecting that the test piece has been inserted into the test piece insertion unit.

Here, whether or not a test piece has been mounted in the apparatus is detected using an insertion/removal detection circuit.

Consequently, when it has been detected that no test piece has been mounted, since the apparatus is not connected to an antenna, the user can be advised that communication is impossible, for example.

The biological sample measurement apparatus according to the seventh invention is the biological sample measurement apparatus according to the sixth invention, further comprising an auxiliary antenna connected to the communication circuit and a communication controller for controlling communication in the communication circuit. The communication controller instructs the communication circuit to retransmit via the auxiliary antenna if communication has not been completed upon detection by the insertion/removal detection circuit that no test piece has been mounted.

Here, in addition to the antenna electrode provided on the side where the test piece is mounted in the apparatus, an auxiliary antenna is provided on the apparatus side. Whether or not a test piece has been mounted is detected, and if none has been mounted, the auxiliary antenna on the apparatus side is used to perform communication again.

Consequently, re-communication can be easily executed using the auxiliary antenna even when a test piece is removed in the midst of the communication of a measurement result or other such information to a data processor or the like, and the communication has not yet been completed.

The biological sample measurement apparatus according to the eighth invention is the biological sample measurement apparatus according to the sixth invention, further comprising a communication controller for controlling communication in the communication circuit. The communication controller instructs the communication circuit to retransmit upon detection of the insertion of the next test piece if communication has not been completed upon detection by the insertion/removal detection circuit that no test piece has been mounted.

Here, when a test piece is removed in the midst of the communication of a measurement result or other such information to a data processor or the like, and the communication has not yet been completed, re-communication is performed after the next test piece has been mounted.

Consequently, even when a test piece is removed in the midst of communication and the communication has not yet been completed, retransmission can be performed automatically by immediately remounting the test piece.

The biological sample measurement apparatus according to the ninth invention is the biological sample measurement apparatus according to any one of the third to eighth inventions, further comprising a display device for displaying the result of measurement by the measurement circuit, and a display controller for controlling the display of the display device. The display controller controls the display device so that the result of measurement is not displayed until the transmission of the measurement result by the communication circuit is complete.

Here, the display device provided on the apparatus side does not allow the measurement result to be displayed until the communication to the data processor or the like is complete.

Consequently, the user can confirm that communication has not been completed until the measurement result is displayed, which prevents the test piece from accidentally being removed from the apparatus during communication.

The biological sample measurement apparatus according to the tenth invention is the biological sample measurement apparatus according to any one of the third to eighth inventions, further comprising a display device for displaying the result of measurement by the measurement circuit, and a display controller for controlling the display of the display device. The display controller controls the display device so that the fact that communication is in progress is displayed until transmission of the result of measurement by the communication circuit is complete.

Here, the display device provided on the apparatus side is controlled so that it displays that the communication is in progress until the communication to the data processor or the like is complete.

Consequently, the user can confirm whether or not communication is in progress just by looking at the display device, which prevents the test piece from accidentally being removed from the apparatus during communication.

Figure 1:
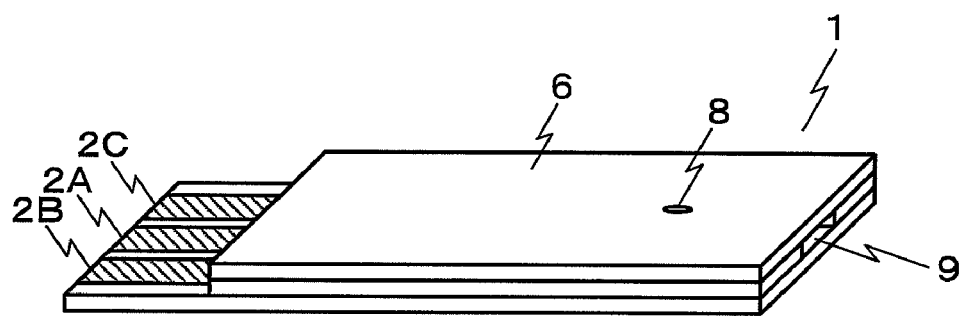
FIG. 1 is an exterior view of a test piece used in a blood glucose measurement device in Embodiment 1 of the present invention.

KEY 1 test piece
2 electrode (measurement electrode)
3 insulated substrate
4 reagent layer
5 spacer
6 cover
7 specimen supply portion 8 air vent
9 blood sample opening
10 test piece insertion unit
11 contact electrode
12 electrode switching circuit
13 CPU (communication controller, display controller)
14 switch
15 communication circuit
16 measurement circuit
17 reference voltage generation circuit
18 current-voltage conversion circuit
19 voltage detection circuit
20 display device
21 memory circuit
22 control switch
23 RF circuit
24 matching circuit
25 case
26 front face
27 rear face
28 upper end face
29 lower end face
30 opening
31 control button
32 battery
33 battery mount
34 substrate
35 insertion/removal detection-use electrode pattern
36 detection-use contact electrode
37 insertion/removal detection circuit
38 buzzer
39 antenna-use electrode pattern (antenna electrode)
50 blood glucose measurement device (biological sample measurement apparatus)
51 measured value display
52 communication state display
53 antenna switch
54 internal antenna
55 internal antenna pattern
150 blood glucose measurement device (biological sample measurement apparatus)

DETAILED DESCRIPTION OF THE PREFERRED EMBODIMENTS

A blood glucose measurement device (biological sample measurement apparatus) 50 that measures a blood glucose value and sends blood glucose value data to the terminal of a computer, a portable terminal apparatus, or the like will be used below as an example of an embodiment of the biological sample measurement apparatus of the present invention, and will be described in detail through reference to the drawings.

Embodiment 1

Figure 2:
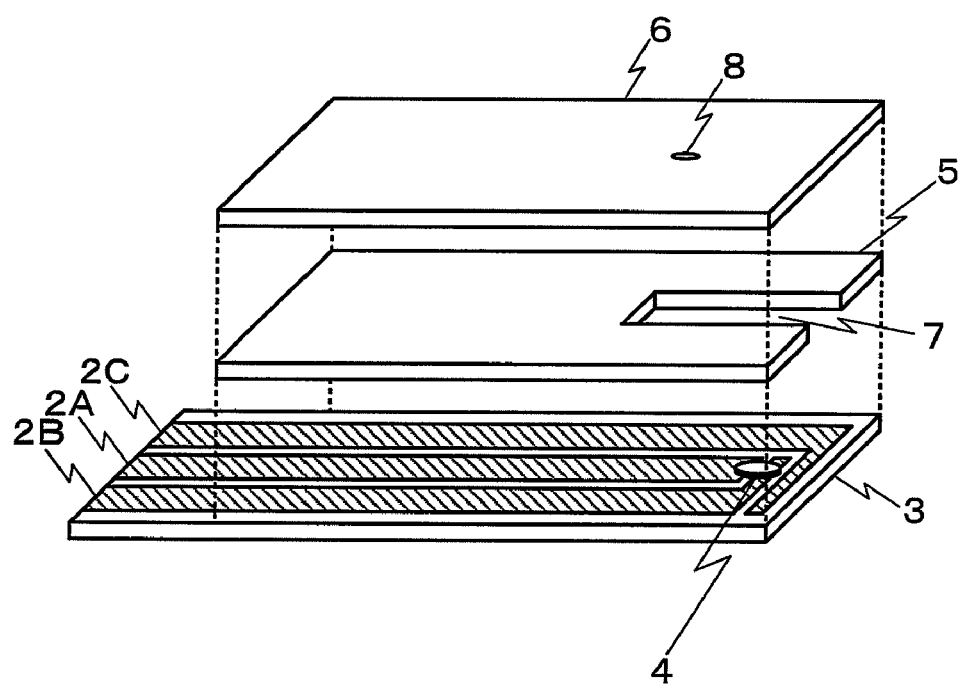
FIG. 2 is an exploded view of a test piece used in a blood glucose measurement device in Embodiment 1 of the present invention.
Figure 3:
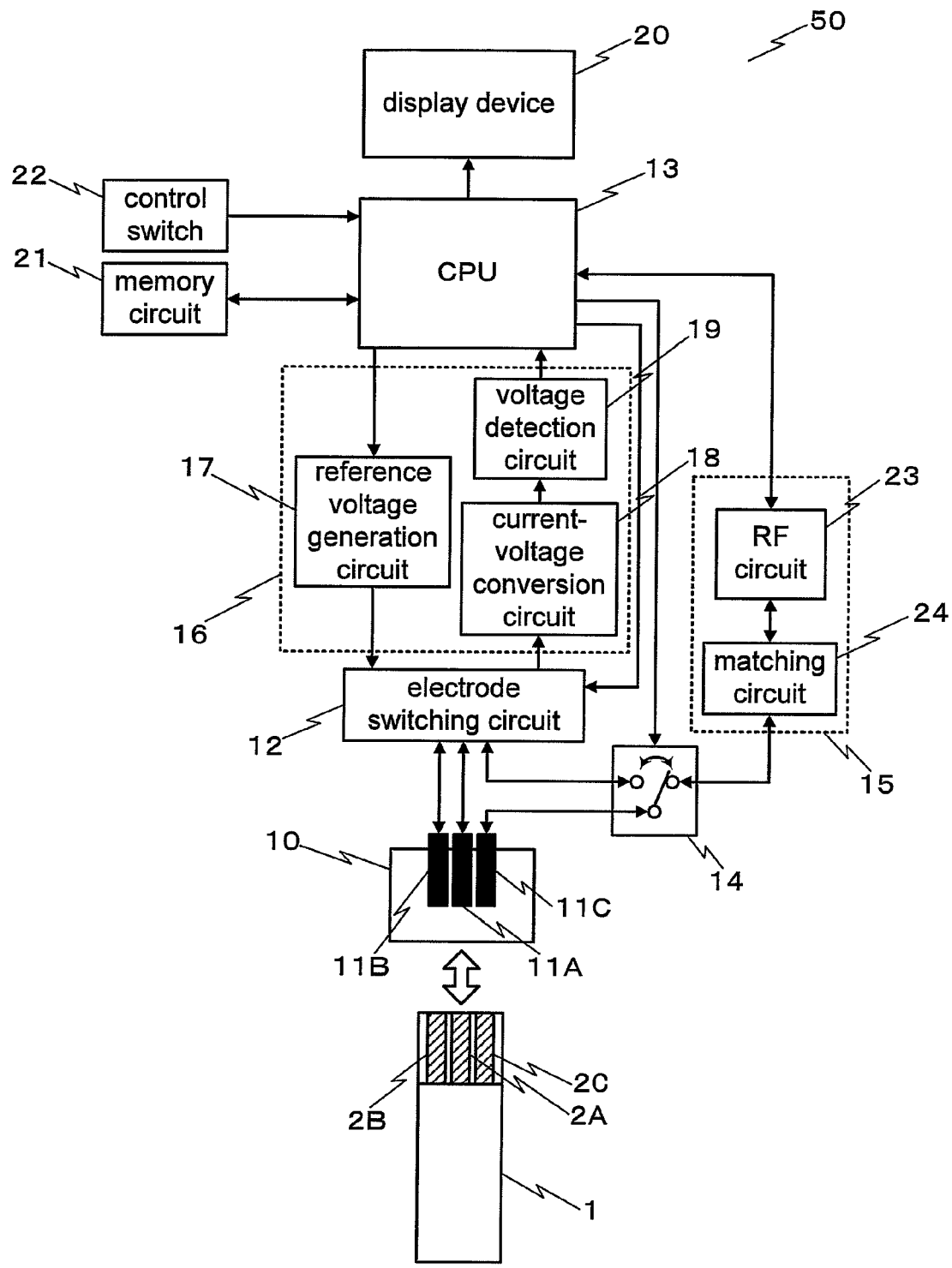
FIG. 3 is a circuit block diagram of a blood glucose measurement device in Embodiment 1 of the present invention.
Figure 4:
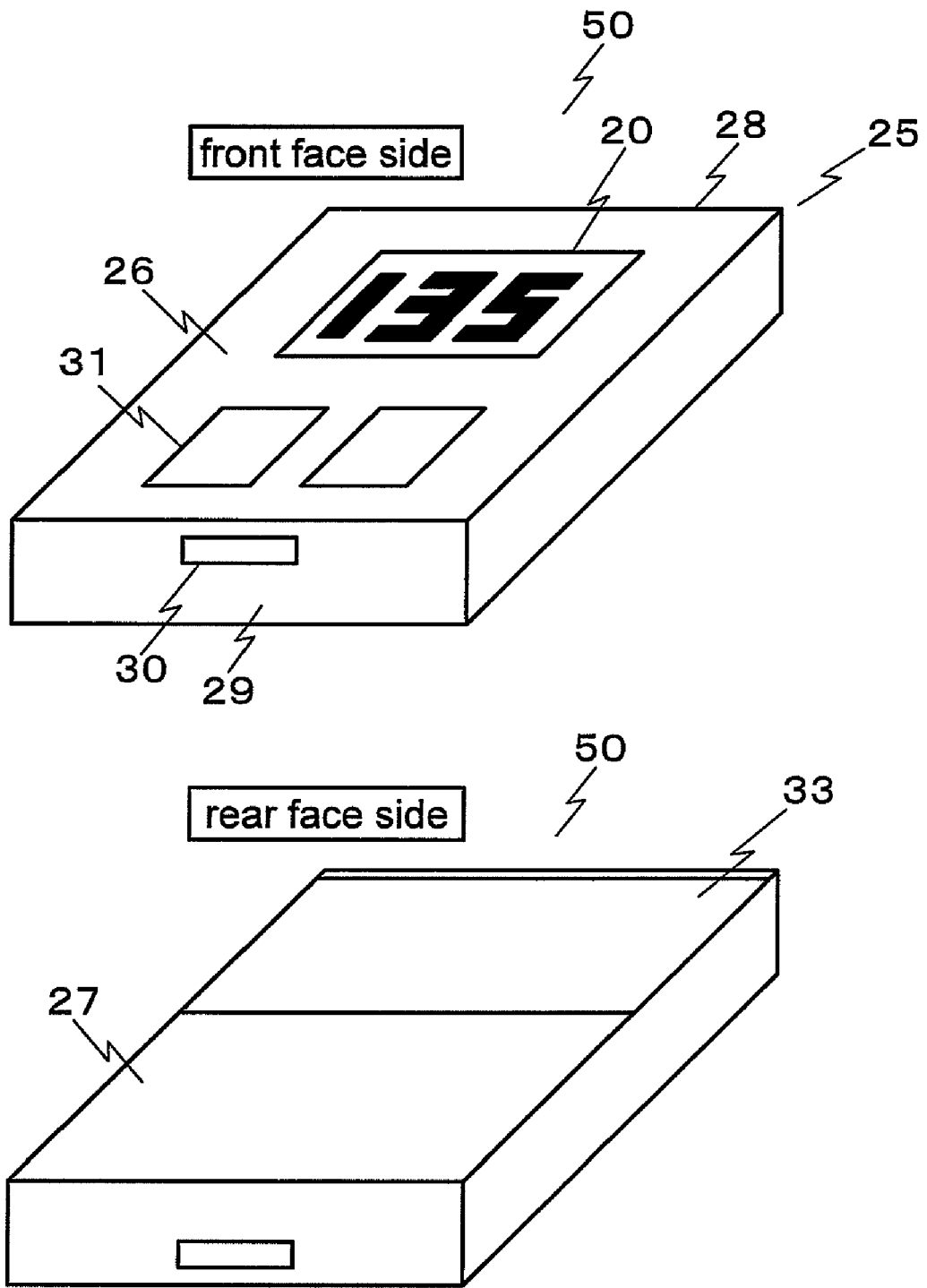
FIG. 4 is an exterior view of a blood glucose measurement device in Embodiment 1 of the present invention.
Figure 5:
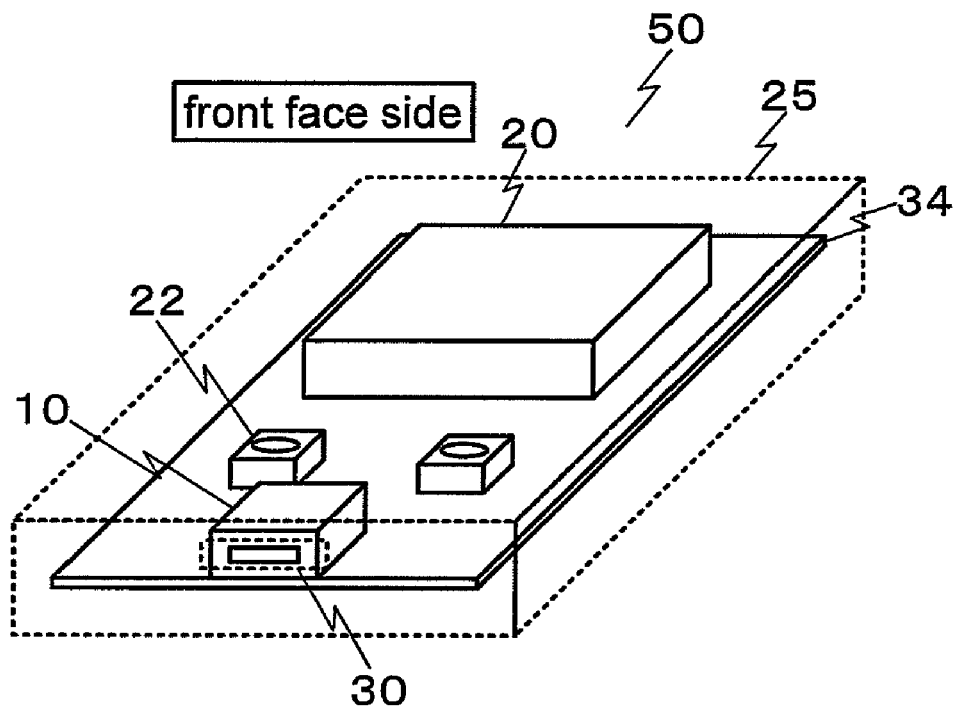
FIG. 5 is a diagram of the internal structure of a blood glucose measurement device in Embodiment 1 of the present invention.
Figure 5:
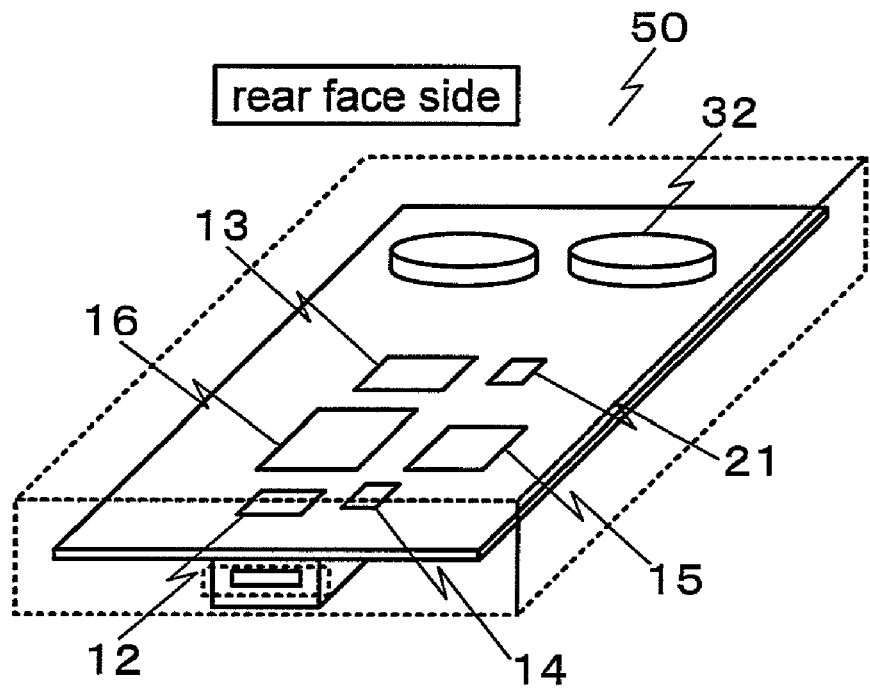
Figure 6:
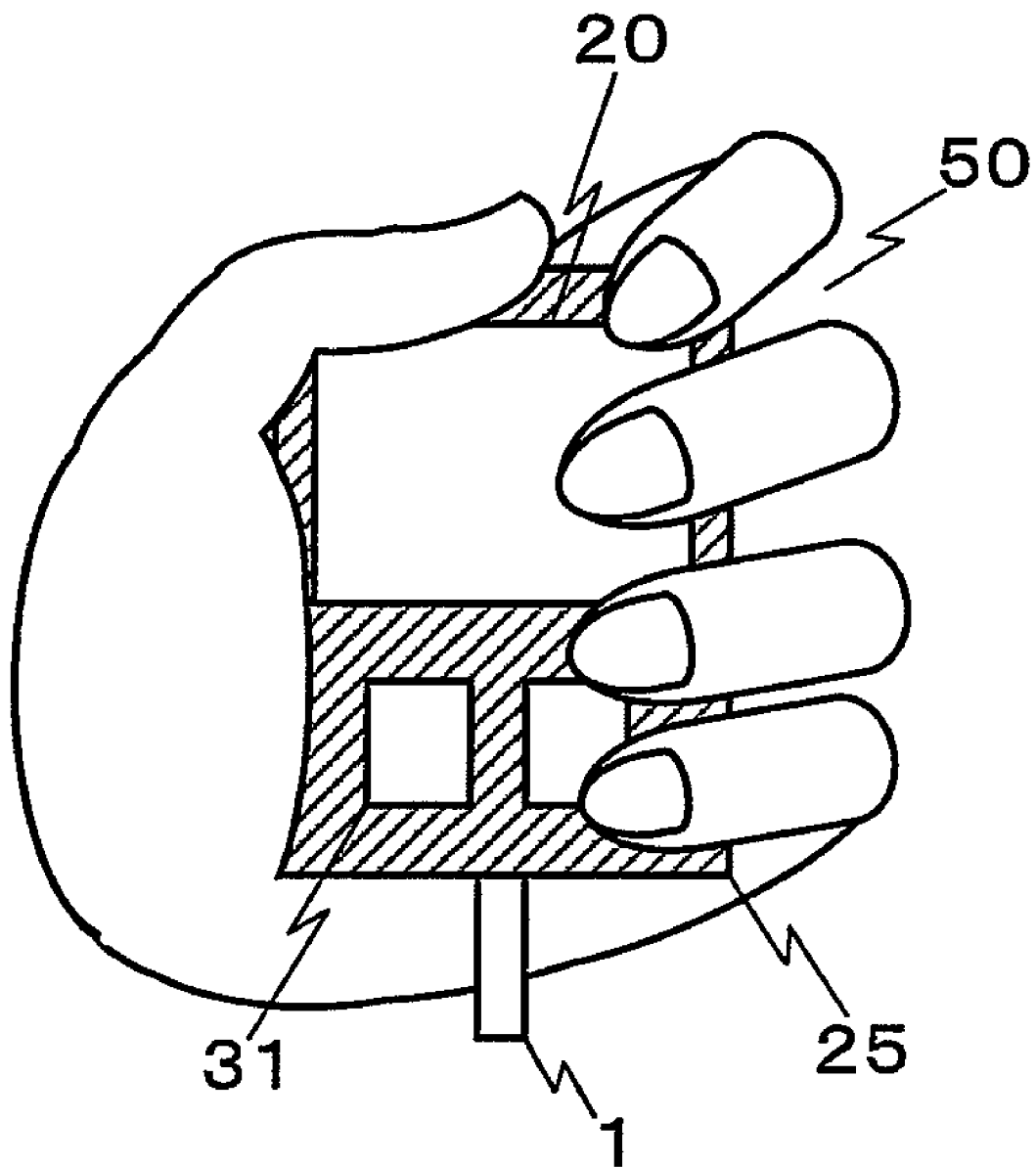
FIG. 6 is a diagram illustrating how a blood glucose measurement device is held in the left hand in Embodiment 1 of the present invention.
Figure 7:
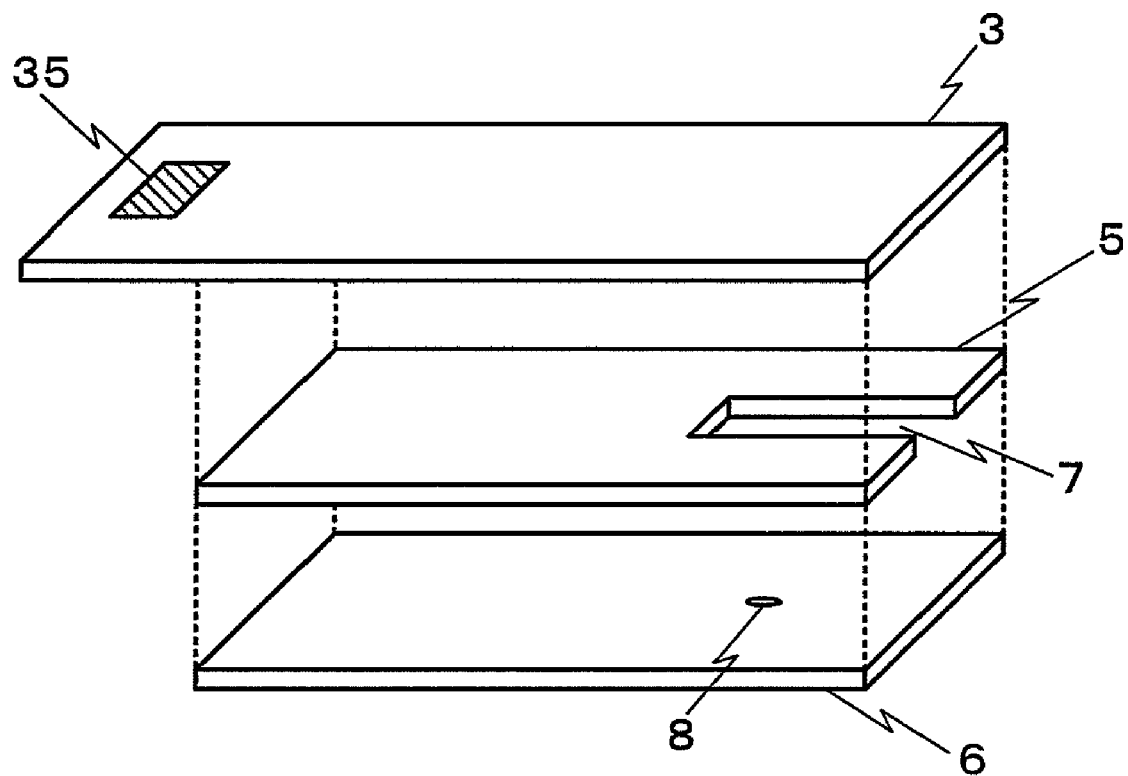
FIG. 7 is an exploded view of when an insertion/removal detection-use electrode pattern was formed on a test piece used in a blood glucose measurement device in Embodiment 1 of the present invention.
Figure 8:
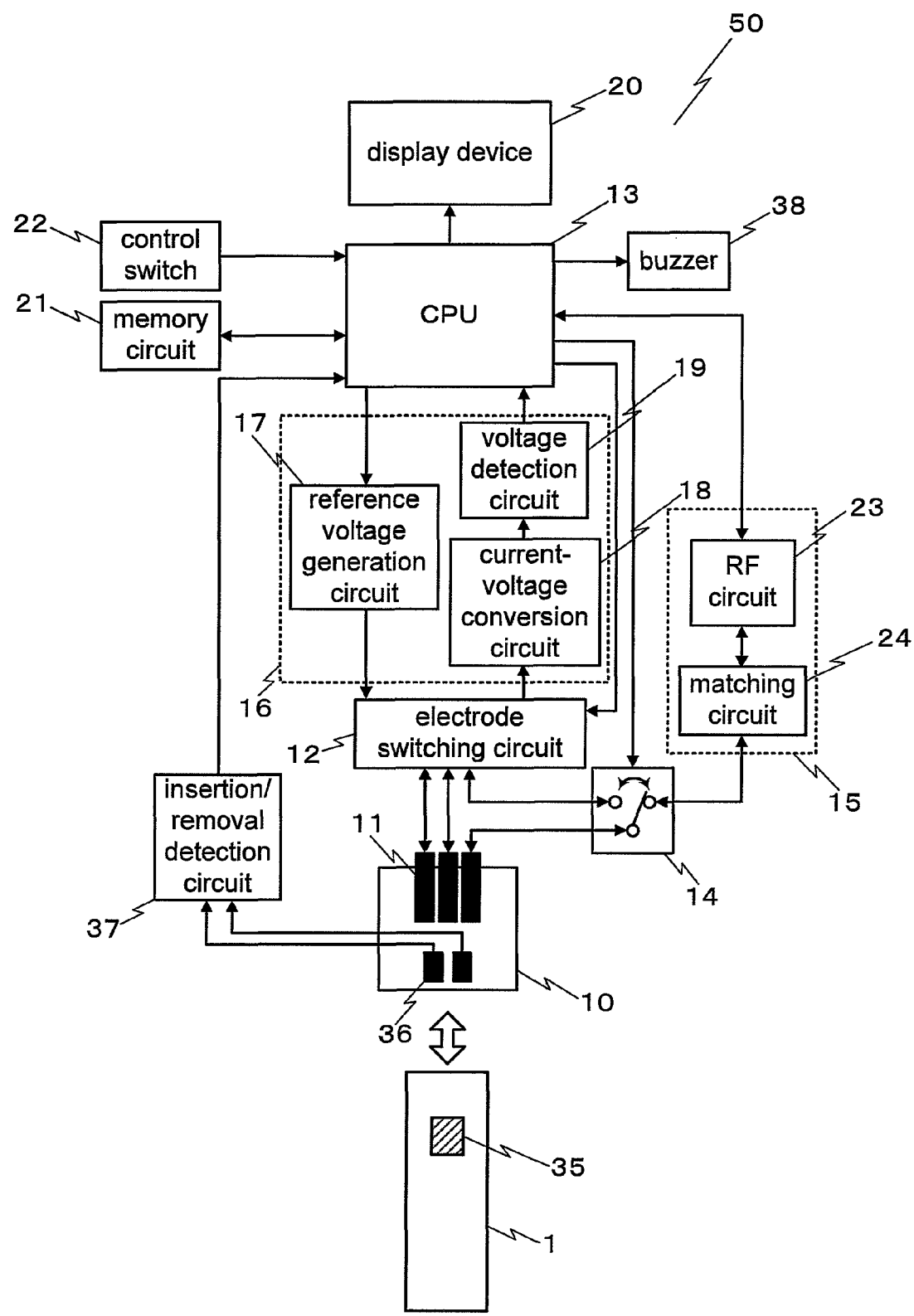
FIG. 8 is a block diagram of a circuit that can detect that a test piece has been pulled out from a blood glucose measurement device in Embodiment 1 of the present invention.

FIG. 1 is an exterior view of a test piece used in a blood glucose measurement device in a first embodiment of the present invention. FIG. 2 is an exploded view of a test piece used in a blood glucose measurement device in the first embodiment of the present invention. FIG. 3 is a circuit block diagram of a blood glucose measurement device in the first embodiment of the present invention. FIG. 4 is an exterior view of a blood glucose measurement device in the first embodiment of the present invention. FIG. 5 is a diagram of the internal structure of a blood glucose measurement device in the first embodiment of the present invention. FIG. 6 is a diagram illustrating how a blood glucose measurement device is held in the left hand in the first embodiment of the present invention. FIG. 7 is an exploded view of when an insertion/removal detection-use electrode pattern was formed on a test piece used in a blood glucose measurement device in the first embodiment of the present invention. FIG. 8 is a block diagram of a circuit that can detect that a test piece has been pulled out from a blood glucose measurement device in the first embodiment of the present invention.

The blood glucose measurement device 50 of this embodiment (see FIGS. 3 and 4, for example) is used by a diabetes patient to measure his or her own blood glucose value. Since measurements must be made several times a day, small and lightweight portable types have become popular because they can be used to take measurements when the patient is away from home. This blood glucose measurement device 50 makes use of an electrochemical system, and involves inserting a disposable test piece 1 into the blood glucose measurement device 50.

First the structure of the test piece 1 will be described through reference to FIGS. 1 and 2.

The test piece 1 mainly comprises a measurement-use electrode pattern (measurement electrode) 2, an insulated substrate 3, a reagent layer 4, a spacer 5, a cover 6, a specimen supply portion 7, an air vent 8, and a blood sample opening 9.

The measurement-use electrode pattern 2 is made up of three electrode patterns 2A, 2B, and 2C, for example, each of which is formed on the insulated substrate 3. The reagent layer 4, which includes a mediator and a redox enzyme such as glucose dehydrogenase, is formed between the measurement-use electrode patterns 2A and 2B.

The spacer 5 is affixed on the side of the insulated substrate 3 where the measurement-use electrode pattern 2 is formed. Since a notch is provided to the spacer 5 here, when the cover 6 is further affixed, this forms the specimen supply portion 7, which has the blood sample opening 9 at one end of the test piece 1.

Also, the air vent 8 is provided to the portion of the cover 6 that touches the specimen supply portion 7, which allows blood to fill the specimen supply portion 7 by capillary action when a drop of blood is placed in the blood sample opening 9. The spacer 5 and the cover 6 are made shorter than the insulated substrate 3. Accordingly, the measurement-use electrode pattern 2 is exposed at the end of the test piece 1 where the blood sample opening 9 is not provided.

Next, the circuit structure of the blood glucose measurement device 50 when the measurement-use electrode pattern 2C is used as an antenna will be described through reference to FIG. 3.

A test piece insertion unit 10 is provided with an insertion opening for inserting the test piece 1, and a contact electrode 11 that comes into contact with the measurement-use electrode pattern 2 exposed on the test piece 1 during insertion.

The contact electrode 11 is made up of three contact electrodes 11A, 11B, and 11C, which respectively come into contact with the measurement-use electrode patterns 2A, 2B, and 2C of the test piece 1 and are electrically connected to each other. Each test piece 1 comes individually wrapped and is taken out of its package immediately before measurement, and inserted into the test piece insertion unit 10. Accordingly, it is unlikely that body oil or dust will adhere to the exposed measurement-use electrode pattern 2, and connection with the contact electrode 11 is possible in a state of low contact resistance. The terminals linked to the contact electrodes 11A and 11B are directly connected to an electrode switching circuit 12. The terminal linked to the contact electrode 11C, on the other hand, is connected via a switch 14 to the electrode switching circuit 12 and a communication circuit 15.

The electrode switching circuit 12 is an analog switch, for example, and the contact electrode 11 connected to a measurement circuit 16 is switched according to commands from a CPU (communication controller, display controller) 13.

The switch 14 is a high-frequency switch, for example, and can transmit high-frequency signals with lower loss than an ordinary analog switch. This switch 14 is preferably a single pole, double throw (SPDT) type of high-frequency switch. In this case, the single pole is connected to the contact electrode 11C, one of two contacts to the electrode switching circuit 12, and the other contact to the communication circuit 15. This switch 14 also switches connections according to commands from the CPU 13.

The measurement circuit 16 is made up of a reference voltage generation circuit 17, a current-voltage conversion circuit 18, and a voltage detection circuit 19.

The reference voltage generation circuit 17 is a D/A converter, for example, with which voltage set to the reference voltage generation circuit 17 by the CPU 13 is applied to the contact electrode 11 via the electrode switching circuit 12 and the switch 14.

The current-voltage conversion circuit 18 is a circuit made up of an Op-Amp and a feedback resistor, for example, with which the value for the current flowing to the feedback resistor from the contact electrode 11 connected by the switch 14 and the electrode switching circuit 12 is converted into a voltage signal, and this voltage is detected by the voltage detection circuit 19 connected to the output side.

The voltage detection circuit 19 is an A/D converter, for example, with which the voltage signal that has undergone digital conversion by the voltage detection circuit 19 is transferred to the CPU 13.

At the CPU 13, computation of the blood glucose value is performed, and the blood glucose value found from this computation is displayed on a display device 20 and stored in a memory circuit 21. The CPU 13 is also connected to a control switch 22, and the reading of the blood glucose value and other such data, operation of the menu screen, and so forth are carried out.

The display device 20 is a liquid crystal monitor, for example, and displays time information, menu screens, and so forth in addition to measurement results.

The memory circuit 21 is an EEPROM, for example, with which blood glucose values, measurement times, and other such data are left as history, and this data can be read out as needed by the user.

The CPU 13 is also connected to the communication circuit 15, allowing the blood glucose value measurement result from the CPU 13 to be sent where desired.

The communication circuit 15 is made up of an RF (radio frequency) circuit 23 and a matching circuit 24.

The RF circuit 23 is made up of an RFIC having a codec function, an error detection function, and a modem function, and peripherals such as a crystal oscillator for generating reference clock of a carrier wave.

The matching circuit 24 is used to perform impedance matching between the measurement-use electrode pattern 2C (antenna) and the transmission path from the RF circuit 23 to the measurement-use electrode pattern 2C, is made up of a capacitor and an inductor, and is optimized according to the frequency band being used. The modulation format is preferably ASK, FSK, PSK, or another such digital modulation format. The frequency band that is used is, for example, the frequency band of short-range wireless assigned to medical use and called the ISM band.

Next, the structure of the blood glucose measurement device 50 will be described through reference to FIGS. 4 and 5. Before moving on to this description, let us define the various faces of the case 25 of the blood glucose measurement device 50. As shown in FIG. 4, the face of the case 25 on which the display device 20 is provided is termed the front face 26, the face on the opposite side from the front face 26 is termed the rear face 27, the end face in the upward direction of the text displayed on the display device 20 is termed the upper end face 28, and the end face in the downward direction of the text displayed on the display device 20 is termed the lower end face 29. To measure a blood glucose value, the test piece 1 is inserted into the blood glucose measurement device 50, and an opening 30 for inserting the test piece 1 is provided to the lower end face 29 of the case 25.

A control button 31 for depressing the control switch 22 is disposed along with the display device 20 on the front face 26 of the case 25. A battery mount 33 for mounting a battery 32 (such as a button battery) is provided to the rear face 27 of the case 25.

The test piece insertion unit 10 is mounted at the end of a substrate 34 so that its insertion opening lines up with the opening 30 inside the case 25.

The electrode switching circuit 12, the CPU 13, the switch 14, the communication circuit 15, the measurement circuit 16, the display device 20, and the memory circuit 21 are mounted on the substrate 34 in addition to the test piece insertion unit 10.

The method for measuring a blood glucose value using the blood glucose measurement device 50 and the test piece 1 constituted as above will now be described.

First, when the test piece 1 is inserted into the test piece insertion unit 10 through the opening 30 provided to the lower end face 29 of the case 25, the blood glucose measurement device 50 enters a state of being ready for measurement.

Next, a spot of blood is placed in the blood sample opening 9 of the test piece 1 exposed through the case 25, and this blood fills the specimen supply portion 7 through capillary action.

The electrode switching circuit 12 and the switch 14 are operated to connect the current-voltage conversion circuit 18 to the contact electrode 11A, and the reference voltage generation circuit 17 to the contact electrode 11C. When voltage is then applied between the measurement-use electrode pattern 2A and the measurement-use electrode pattern 2C, and the blood fills the specimen supply portion 7, the value of the current flowing between the electrodes changes. Accordingly, the filling with blood can be detected by detecting this change in the current value with the current-voltage conversion circuit 18, the voltage detection circuit 19, and the CPU 13.

Next, after the blood filling the specimen supply portion 7 has reacted for a specific length of time with the reagent layer 4, the electrode switching circuit 12 is operated to connect the current-voltage conversion circuit 18 to the contact electrode 11A, and the reference voltage generation circuit 17 to the contact electrode 11B. When voltage is then applied between the measurement-use electrode pattern 2A and the measurement-use electrode pattern 2B, current that is proportional to the glucose content flows between the electrodes. Accordingly, this current value can be detected with the current-voltage conversion circuit 18, the voltage detection circuit 19, and the CPU 13.

Next, the electrode switching circuit 12 is operated to connect the reference voltage generation circuit 17 to the contact electrode 11A, and the current-voltage conversion circuit 18 to the contact electrode 11C. When voltage is then applied between the measurement-use electrode pattern 2A and the measurement-use electrode pattern 2C, current that is proportional to a Hct (hematocrit) value flows between the electrodes. Accordingly, this current value can be detected with the current-voltage conversion circuit 18, the voltage detection circuit 19, and the CPU 13.

Finally, the glucose content converted from the current value is corrected by the CPU 13 from the Hct value converted from the current value, to compute the blood glucose value.

The blood glucose value data measured as above is transferred to the RF circuit 23 along with time information and the ID of the blood glucose measurement device 50.

The RF circuit 23 encodes the data acquired from the CPU 13, adds error detection codes, and performs modulation. The signal modulated by the RF circuit 23 is sent when a transmission request command is sent from the CPU 13 to the RF circuit 23. After this, the modulated signal is supplied through the matching circuit 24 to the measurement-use electrode pattern 2C (antenna), and radio waves are emitted from the measurement-use electrode pattern 2C. The switch 14 at this point is switched so as to connect the contact electrode 11C and the communication circuit 15.

The size of the blood glucose measurement device 50 will vary with the manufacturer and the model, but as shown in FIG. 6, it is usually small enough to be held in one hand by an adult. Therefore, depending on the size of the user's hand, it is conceivable that the majority of the blood glucose measurement device 50 will be covered by the hand in which it is held. In this case, there is the possibility that most of the radio waves emitted will end up being absorbed by the user's hand, preventing the data from being transmitted properly.

The test piece 1 is inserted into the test piece insertion unit 10 so that the end on which the blood sample opening 9 is provided protrudes from the opening 30 provided to the lower end face 29 of the case 25, so that a spot of blood can be placed in a state in which the test piece 1 has been inserted into the blood glucose measurement device 50. The blood adheres to the blood sample opening 9 located at the protruding distal end of the test piece 1 and to the surrounding area. Therefore, the user usually holds the blood glucose measurement device 50 while avoiding the area around the protruding distal end of the test piece 1 so as to avoid getting blood on his or her hand.

If the hand should come into contact with the protruding test piece 1, this may hamper the contact between the contact electrode 11 provided to the test piece insertion unit 10 and the measurement-use electrode pattern 2 formed on the test piece 1, resulting in erroneous measurement of the blood glucose value, or causing the test piece 1 to fall out. Accordingly, the user usually holds the blood glucose measurement device 50 at a place away from the area around the protruding test piece 1.

In other words, if the measurement-use electrode pattern 2C formed on the test piece 1 is used as an antenna, the effect of radio wave absorption by the user's hand will be less significant than when the antenna is provided on the inside of the case 25. Thus, using the measurement-use electrode pattern 2C formed on the test piece 1 as an antenna ensures good transmission performance.

When the measurement-use electrode pattern 2C is used as an antenna, the switch 14 is operated so that the contact electrode 11C and the communication circuit 15 are connected. When this is done, the communication circuit 15 and the measurement-use electrode pattern 2C are connected and the measurement-use electrode pattern 2C can be used as an antenna. The switching of the switch 14 is controlled by the CPU 13. Upon completion of the computation of the blood glucose value, the CPU 13 sends out a switching command so that the contact electrode 11C and the communication circuit 15 are connected.

When the measurement-use electrode pattern 2C formed on the test piece 1 is used as an antenna as above, it is conceivable that the test piece 1 could be pulled out in the midst of data transfer, thereby making communication impossible. However, since the data being sent is mainly blood glucose values, the ID of the blood glucose measurement device 50, and time information, the amount of data is small and transmission is completed in a short time. Accordingly, if transmission is performed as soon as the blood glucose value has been measured, it is unlikely that this problem will occur.

If the test piece 1 should happen to be pulled out during data transmission, though, it is preferable if this is detected and a request is made to the user to reinsert the test piece 1 and send the data once more.

The structure of the test piece 1 and the blood glucose measurement device 50 in this case will now be described through reference to FIGS. 7 and 8.

As shown in FIG. 7, an insertion/removal detection-use electrode pattern 35 is provided to the side of the insulated substrate 3 of the test piece 1 on which the measurement-use electrode pattern 2 is not formed. As shown in FIG. 8, a detection-use contact electrode 36 is provided to the test piece insertion unit 10 for making contact with the insertion/removal detection-use electrode pattern 35 and electrically connecting it when the test piece 1 has been inserted into the test piece insertion unit 10.

The detection-use contact electrode 36 is made up of two electrodes, and when the test piece 1 has been inserted into the test piece insertion unit 10, the two electrodes of the detection-use contact electrode 36 are short-circuited by the insertion/removal detection-use electrode pattern 35 of the test piece 1.

The detection-use contact electrode 36 is connected to an insertion/removal detection circuit 37.

The insertion/removal detection circuit 37 outputs a high or low signal according to whether the two electrodes of the detection-use contact electrode 36 are open or shorted. It can be detected that the test piece 1 has been pulled out by monitoring the output of the insertion/removal detection circuit 37 with the CPU 13.

If the insertion/removal detection circuit 37 detects that the test piece 1 has been pulled out during data transmission, the communication circuit 15 determines whether or not the data transmission was completed. Here, if the transmission was not completed, the transmission data is stored, and the data is resent when the test piece 1 has been reinserted. Also, the CPU 13 sounds an alarm with a connected buzzer 38, and instructs the display device 20 to put up a display recommending reinsertion.

As discussed above, in this embodiment, the measurement-use electrode pattern 2C formed on the test piece 1 is used as the antenna of the communication circuit 15. Accordingly, the effect of radio wave absorption caused by the antenna portion being covered by the hand in which the blood glucose measurement device 50 is held is reduced, so the radio waves can be emitted more efficiently into the space where communication is supposed to take place. As a result, transmission power can be kept low.

Figure 12:
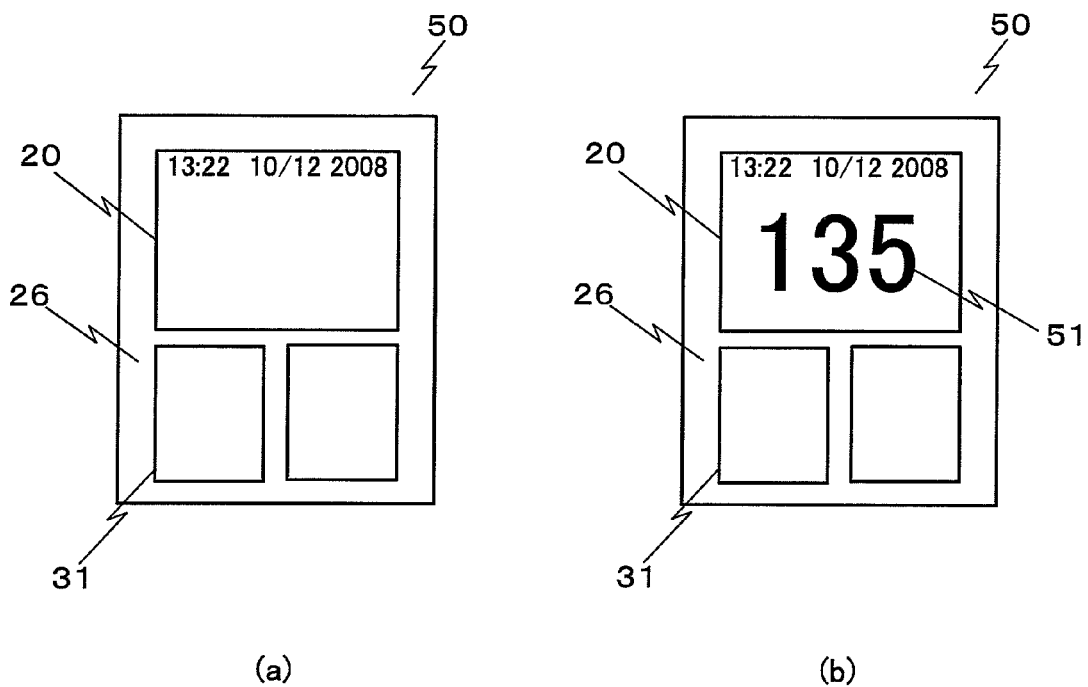
FIGS. 12A and 12B illustrate an example of the change in the display state of a blood glucose measurement device according to another embodiment of the present invention.

The structure may be such that the display device 20 does not display the measurement result sent from the CPU 13 until the transmission of the measurement result is complete in the communication circuit 15, as shown in FIG. 12A, but when this transmission is complete, as shown in FIG. 12B, the result is displayed on a measured value display 51.

Figure 13:
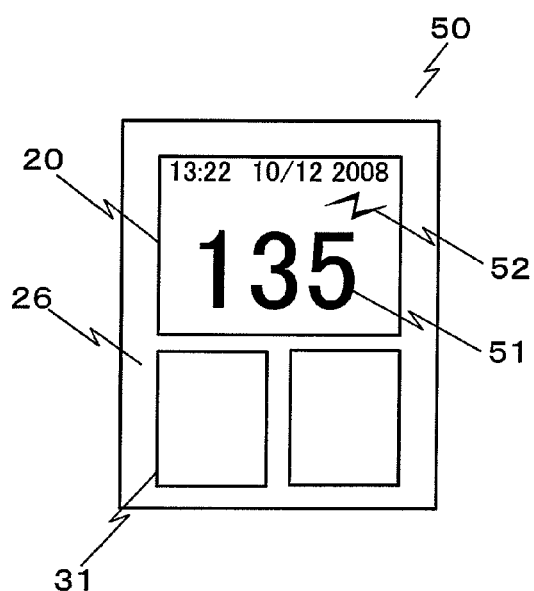
FIG. 13 illustrates another example of the display state of a blood glucose measurement device according to another embodiment of the present invention.

Alternatively, the structure may be such that until the transmission of the measurement result is complete in the communication circuit 15, as shown in FIG. 13, the display device 20 displays a communication state display 52 which means that communication is in progress, along with the measured value display 51.

As discussed above, the CPU 13 sends the measured blood glucose value to the display device 20 and the communication circuit 15. In addition, the CPU 13 monitors whether or not the transmission of the measured blood glucose value has been completed by the communication circuit 15, and if this transmission is complete, the display device 20 is notified to that effect. The display device 20 is controlled by the CPU 13 (see FIG. 12A) so that the display of the blood glucose value, that is, the display of the measured value display 51 (see FIG. 12B), is not performed from the time when the blood glucose value is sent from the CPU 13 until the communication is completed. Alternatively, the display device 20 is controlled by the CPU 13 (see FIG. 13) so that the blood glucose value is displayed and the communication state display 52 which means that communication is in progress is also displayed. Accordingly, the user can be notified of whether or not communication has been completed, and can therefore be urged not to pull the test piece 1 out of the test piece insertion unit 10 until the communication is complete.

Although not depicted in the circuit structure of FIG. 8, the blood glucose measurement device 50 of this embodiment may be equipped with an internal antenna connected to the communication circuit 15.

Figure 14:
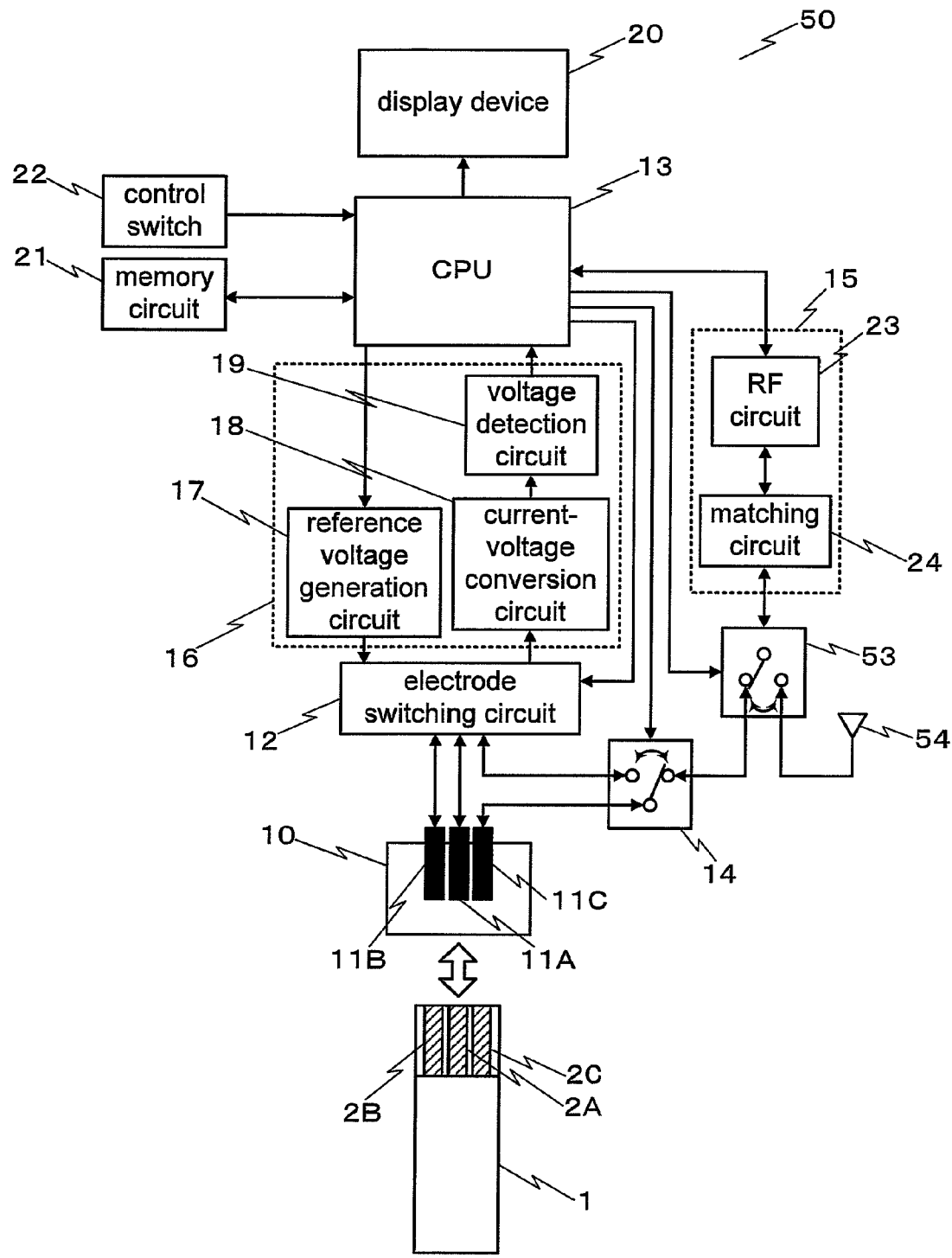
FIG. 14 is a circuit block diagram illustrating a structure for performing communication using an internal antenna built into a blood glucose measurement device according to another embodiment of the present invention.

The communication circuit 15 usually performs communication by using the measurement-use electrode pattern in the test piece 1 as an antenna. Here, the CPU 13 sends a detection result to the communication circuit 15 when the insertion/removal detection circuit 37 detects that the test piece 1 has been pulled out of the test piece insertion unit 10. If the communication circuit 15 has not yet completed communication upon receipt of this notification, the CPU 13 switches an antenna switch (high-frequency switch) 53 as shown in FIG. 14, and uses an internal antenna 54 inside the blood glucose measurement device 50 to perform communication again. The internal antenna 54 in the blood glucose measurement device 50 here is constituted by an antenna pattern, a chip antenna, or the like.

Consequently, even if the test piece 1 should be pulled out of the test piece insertion unit 10 during communication or before communication has been performed, it will still be possible to send the measurement result. Also, only at this time, the communication circuit 15 increases the transmission power to perform communication, but the transmission power is kept low under normal circumstances when communication is performed using the test piece 1 as an antenna, so the object of the present invention can be achieved.

Embodiment 2

Figure 9:
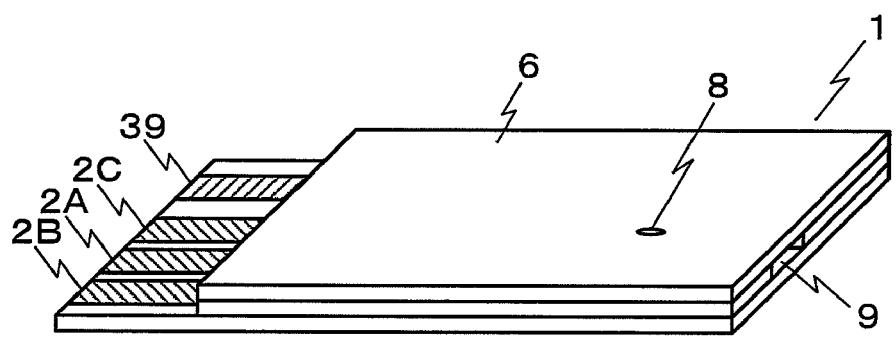
FIG. 9 is an exterior view of when an antenna-use electrode pattern was formed on a test piece used in a blood glucose measurement device in Embodiment 2 of the present invention.
Figure 10:
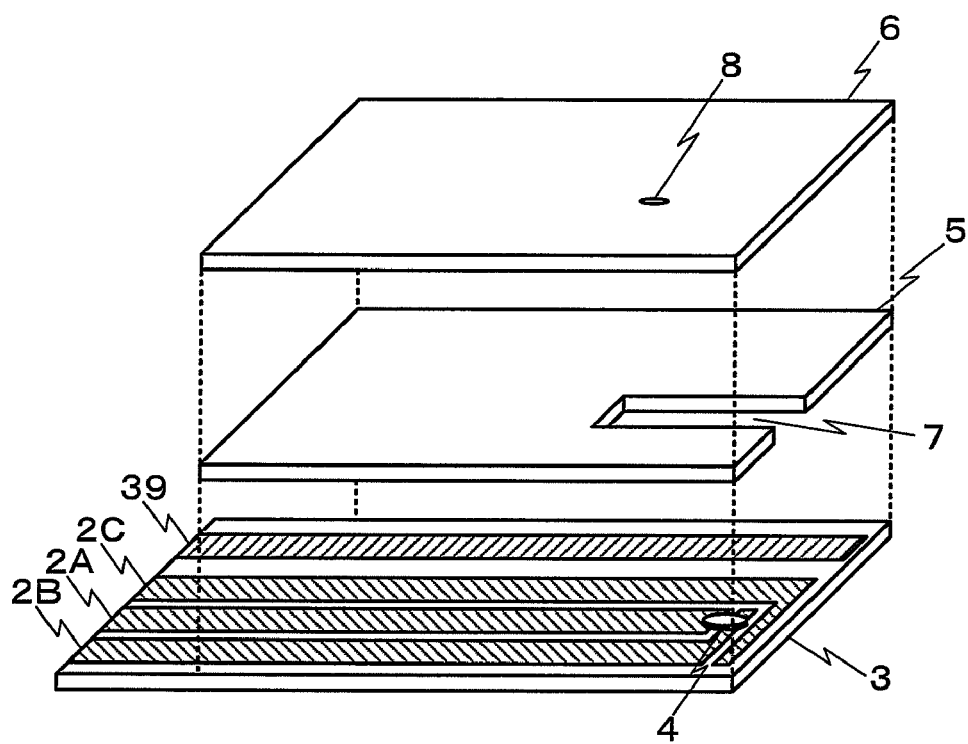
FIG. 10 is an exploded view of when an antenna-use electrode pattern was formed on a test piece used in a blood glucose measurement device in Embodiment 2 of the present invention.
Figure 11:
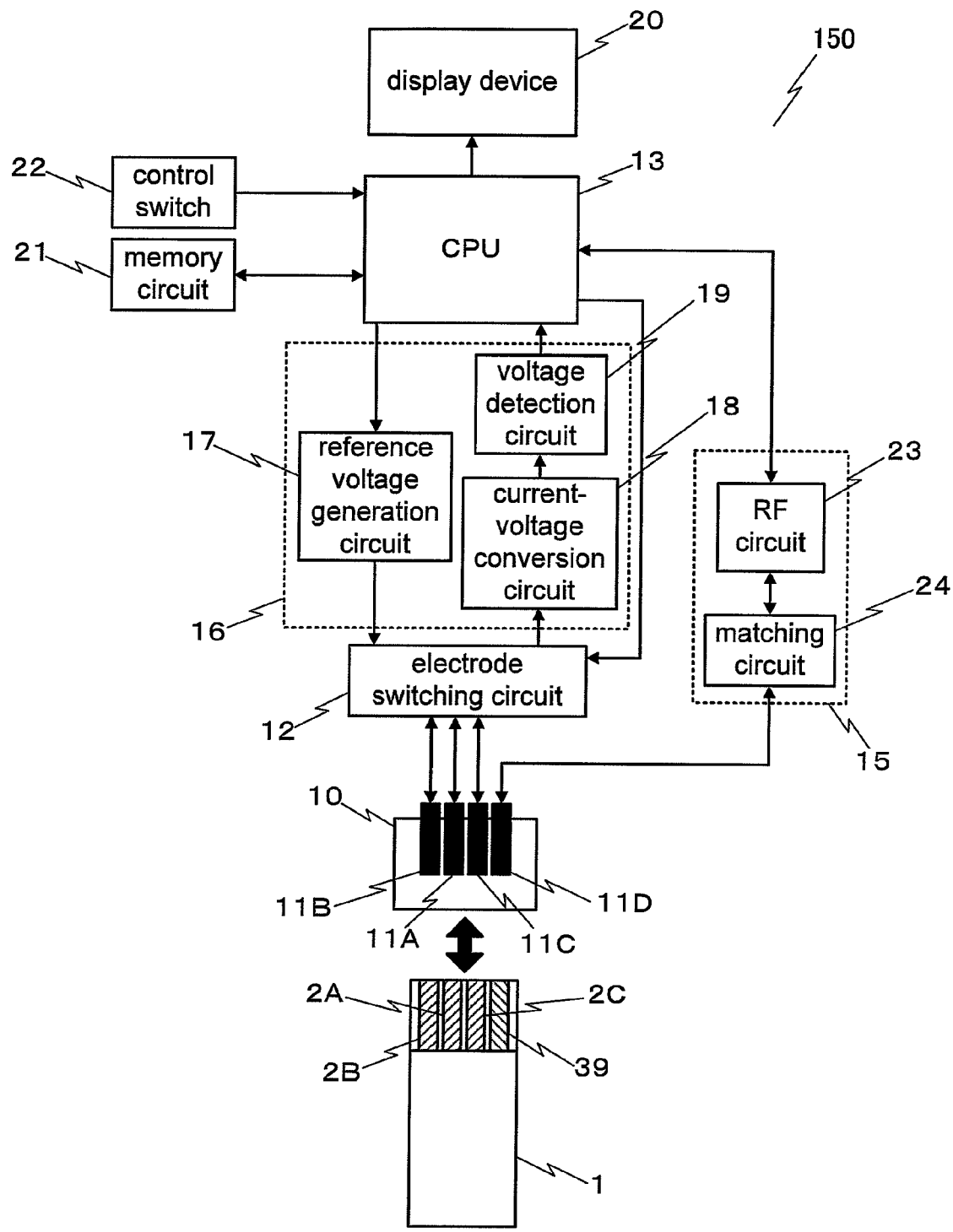
FIG. 11 is a circuit block diagram when an antenna-use electrode pattern of a blood glucose measurement device is used as an antenna in Embodiment 2 of the present invention.

FIG. 9 is an exterior view of when an antenna-use electrode pattern was formed on a test piece used in a blood glucose measurement device 150 (see FIG. 11) in Embodiment 2 of the present invention. FIG. 10 is an exploded view of when an antenna-use electrode pattern was formed on a test piece used in the blood glucose measurement device 150 (see FIG. 11) in Embodiment 2 of the present invention. FIG. 11 is a circuit block diagram when an antenna-use electrode pattern of the blood glucose measurement device 150 (see FIG. 11) is used as an antenna in Embodiment 2 of the present invention.

First, the structure of the test piece 1 will be described through reference to FIGS. 9 and 10.

This embodiment (FIGS. 9 and 10) differs from the constitution of Embodiment 1 above (FIGS. 1 and 2) in that an antenna-use electrode pattern (antenna electrode) 39 is provided to the test piece 1. Therefore, here we will only describe the differences from Embodiment 1 above, and the rest of the constitution will not be described again.

The antenna-use electrode pattern 39 is formed on the insulated substrate 3 in the same manner as the measurement-use electrode pattern 2, but it is preferably formed at a location where it will not come into contact with the specimen supply portion 7, so as not to affect the measurement result for the blood glucose value. Also, the antenna-use electrode pattern 39 is similar to the measurement-use electrode pattern 2 in that it is exposed at the end of the test piece 1 where the blood sample opening 9 is not formed.

Next, the circuit structure of the blood glucose measurement device 150 when the antenna-use electrode pattern 39 is used as an antenna will be described through reference to FIG. 11. This embodiment (FIG. 11) differs from the constitution of Embodiment 1 above (FIG. 3) in that the antenna-use electrode pattern 39 is used instead of the measurement-use electrode pattern 2C as the antenna for the communication circuit 15. Therefore, we will only describe the changes made to the constitution of Embodiment 1 above (FIG. 3) by using the antenna-use electrode pattern 39 as the antenna for the communication circuit 15.

The test piece insertion unit 10 comprises an insertion opening for inserting the test piece 1, and the contact electrode 11 that is in contact with the antenna-use electrode pattern 39 and the measurement-use electrode pattern 2 exposed on the test piece 1 during insertion.

The contact electrode 11 is made up of four contact electrodes 11A, 11B, 11C, and 11D. The contact electrodes 11A, 11B, and 11C come into contact with the measurement-use electrode patterns 2A, 2B, and 2C of the test piece 1, while the contact electrode 11D comes into contact with the antenna-use electrode pattern 39, so that they are electrically connected to each other. Each test piece 1 comes individually wrapped and is taken out of its package immediately before measurement, and inserted into the test piece insertion unit 10. Accordingly, it is unlikely that body oil or dust will adhere to the exposed measurement-use electrode pattern 2 and the antenna-use electrode pattern 39, and connection with the contact electrode 11 is possible in a state of low contact resistance.

The terminals linked to the contact electrodes 11A, 11B, and 11C are connected to the electrode switching circuit 12, and the terminal linked to the contact electrode 11D is connected to the communication circuit 15. The communication circuit 15 has an RF circuit 23 and a matching circuit 24.

The matching circuit 24 is used to perform impedance matching between the antenna-use electrode pattern 39 (antenna) and the transmission path from the RF circuit 23 to the antenna-use electrode pattern 39. Also, the matching circuit 24 is configured so as to include a capacitor and an inductor, and is optimized according to the frequency band being used.

Because of the constitution in this embodiment, there is the danger that the radio waves emitted from the antenna-use electrode pattern 39 will generate an induced electromotive force in the measurement-use electrode pattern 2 and affect the measurement result for the blood glucose value. Thus, the transmission function of the RF circuit 23 is halted during measurement of the blood glucose value.

The method for measuring a blood glucose value when using the blood glucose measurement device 150 and the test piece 1 constituted as above is the same as in Embodiment 1, and so will not be described again.

Figure 15:
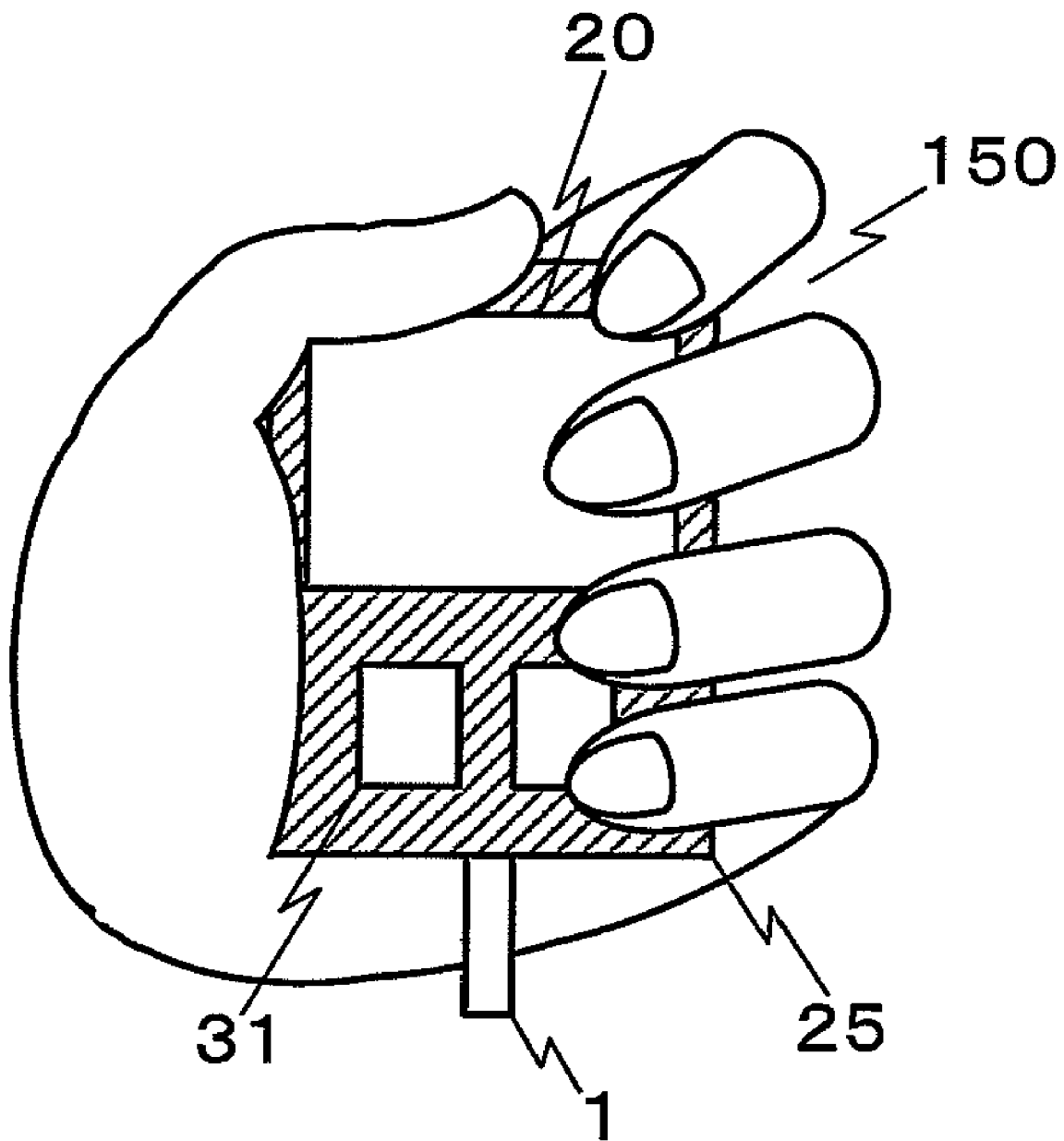
FIG. 15 illustrates how the blood glucose measurement device in FIG. 11 is held in the left hand.

The size of the blood glucose measurement device 150 will vary with the manufacturer and the model, but as shown in FIG. 15, it is usually designed to be small enough to be held in one hand by an adult. Therefore, depending on the size of the user's hand, it is conceivable that the majority of the blood glucose measurement device 150 will be covered by the hand in which it is held. In this case, there is the possibility that most of the radio waves emitted will end up being absorbed by the user's hand, preventing the data from being transmitted properly.

The test piece 1 is inserted into the test piece insertion unit 10 so that the end on which the blood sample opening 9 is provided protrudes from the opening 30 provided to the lower end face 29 of the case 25, so that a spot of blood can be placed in a state in which the test piece 1 has been inserted into the blood glucose measurement device 150. The blood adheres to the blood sample opening 9 located at the protruding distal end of the test piece 1 and to the surrounding area. Therefore, the user usually holds the blood glucose measurement device 150 while avoiding the area around the protruding distal end of the test piece 1 so as to avoid getting blood on his or her hand.

If the hand should come into contact with the protruding test piece 1, this may hamper the contact between the contact electrode 11 provided to the test piece insertion unit 10 and the measurement-use electrode pattern 2 formed on the test piece 1, resulting in erroneous measurement of the blood glucose value, or causing the test piece 1 to fall out. Accordingly, the user usually holds the blood glucose measurement device 150 at a place away from the area around the protruding test piece 1. In other words, if the antenna-use electrode pattern 39 formed on the test piece 1 is used as an antenna, the effect of radio wave absorption by the user's hand will be less significant than when the antenna is provided on the inside of the case 25. As a result, the radio waves will be emitted from the test piece side more efficiently. Thus, using the antenna-use electrode pattern 39 formed on the test piece 1 as an antenna ensures good transmission performance.

When the antenna-use electrode pattern 39 formed on the test piece 1 is used as an antenna as above, it is conceivable that the test piece 1 could be pulled out in the midst of data transfer, thereby making communication impossible. However, since the data being sent is mainly blood glucose values, the ID of the blood glucose measurement device 150, and time information, the amount of data is small and transmission is completed in a short time. Accordingly, if transmission is performed as soon as the blood glucose value has been measured, it is unlikely that this problem will occur.

If the test piece 1 should happen to be pulled out during data transmission, it is preferable for the constitution to be such that it is detected that the test piece 1 has been pulled during data transmission, and a request is made to the user to reinsert the test piece 1 and send the data once more. This constitution is the same as that in Embodiment 1 (FIGS. 7 and 8), and so will not be described again.

As mentioned above, with this embodiment, the antenna-use electrode pattern 39 formed on the test piece 1 is used as an antenna for the communication circuit 15. Consequently, the effect of radio wave absorption caused by the antenna portion being covered by the hand in which the blood glucose measurement device 150 is held is reduced, so the radio waves can be emitted more efficiently into the space where communication is supposed to take place. As a result, transmission power can be kept low.

Other Embodiments (A)

Embodiments 1 and 2 above were described using examples in which the blood glucose measurement devices 50 and 150 were used as the biological sample measurement apparatus, but the present invention is not limited to this.

For instance, the measurement apparatus may be one that measures lactic acid, uric acid, or the like, and what is measured is not really important as long as the apparatus is one that measures after the test piece 1 has been inserted into the apparatus.

(B)

Embodiments 1 and 2 above were described using examples in which the opening 30 was provided to the lower end face 29 of the case 25, but the present invention is not limited to this.

The location where the opening 30 is provided is preferably dictated by the object of communication.

For example, if the object of communication is a base station disposed away from the user, or a PC or other such data management terminal, the test piece 1 is preferably disposed at the location farthest away from the user's body in order to minimize the effect of radio wave absorption into the user's body. To this end, a constitution is preferable in which the opening 30 is provided to the upper end face 28 of the case 25, and the test piece 1 is inserted into this opening 30.

(C)

As described in Embodiment 1 above, the display device 20 may not display the measurement result sent from the CPU 13 until the completion of the transmission of the measurement result by the communication circuit 15, or may display that communication is in progress.

As discussed above, the CPU 13 sends the measured blood glucose value to the display device 20 and the communication circuit 15. In addition, the CPU 13 also monitors whether or not the communication circuit 15 has completed transmission of the measured blood glucose value, and once this transmission is complete, notifies the display device 20 to this effect. The display device 20 does not display the blood glucose value until the blood glucose value has been sent from the CPU 13, and it has then been notified that communication is complete, or displays the blood glucose value and also displays that communication is in progress.

Accordingly, the user can be informed that communication has been completed, and therefore can be advised not to pull the test piece 1 out of the test piece insertion unit 10 until the communication is complete.

(D)

Also, although not depicted in the drawings, with the circuit structure in FIG. 11, the blood glucose measurement device 150 of the present invention equipped with the insertion/removal detection circuit 37 discussed in Embodiment 1 into the components of the Embodiment 2 discussed above may be equipped with an internal antenna connected to the communication circuit 15.

Usually, the communication circuit 15 performs communication using the antenna-use electrode pattern 39 of the test piece 1. Here, the CPU 13 notifies the information to the communication circuit 15 when the insertion/removal detection circuit 37 detects that the test piece 1 has been pulled out of the test piece insertion unit 10. The communication circuit 15 uses the antenna in the blood glucose measurement device 150 to perform communication again if the communication has not been completed at the point of this notification.

Here, the antenna in the blood glucose measurement device 150 is constituted by a pattern antenna, a chip antenna, or the like.

Consequently, even if the test piece 1 should be pulled out of the test piece insertion unit 10 during communication or before communication has been performed, it will still be possible to send the measurement result.

Also, only at this time, the communication circuit 15 increases the transmission power to perform communication, but the transmission power is kept low under normal circumstances when communication is performed using the test piece 1 as an antenna, so the object of the present invention can be achieved.

(E)

Figure 16:
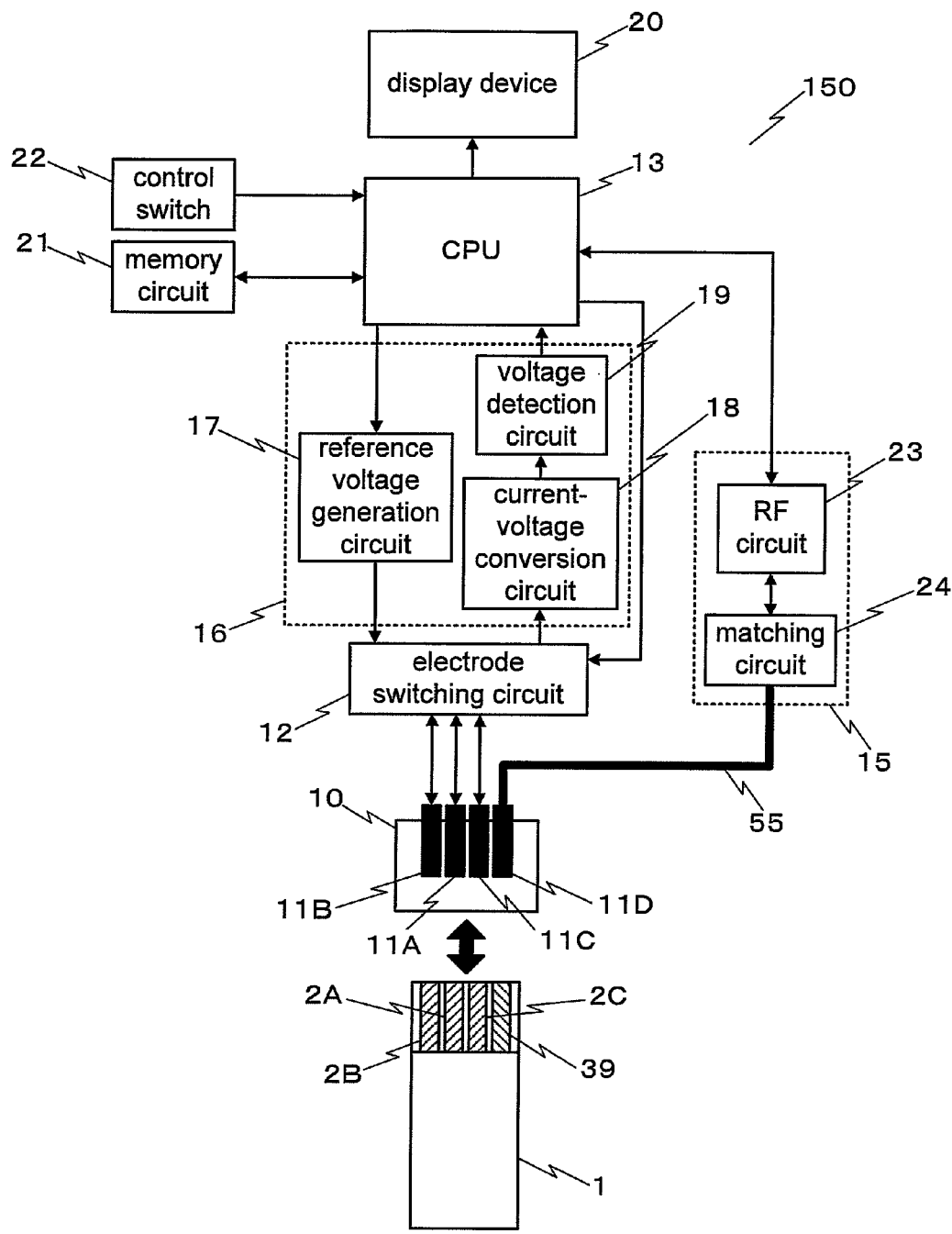
FIG. 16 is a circuit block diagram illustrating the structure of a blood glucose measurement device that includes an internal antenna pattern in an apparatus according to yet another embodiment of the present invention.

Also, although not depicted in the drawings, with the circuit structure in FIG. 11, an antenna pattern 55 may be formed between the contact electrode 11D in the test piece insertion unit 10 and the communication circuit 15 as shown in FIG. 16, so when the test piece 1 is inserted into the test piece insertion unit 10, the antenna-use electrode pattern 39 and this antenna pattern 55 operate as an integrated antenna.

Doing this allows the antenna to be made longer, which makes it possible to expand the frequency band over which communication is performed.

Other Effects

With the biological sample measurement apparatus and test piece for measuring a biological sample of the present invention, the effect of radio wave absorption by the user's hand is reduced, so radio waves are emitted more efficiently and the transmission power can be kept low.

In turn, keeping the transmission power low means that the biological sample measurement apparatus will consume less power, and the battery will last longer.

Furthermore, the reduction is size that accompanies a reduction in battery capacity means that the biological sample measurement apparatus can be smaller and lighter in weight.

INDUSTRIAL APPLICABILITY

With the biological sample measurement apparatus and the test piece for measuring a biological sample according to the present invention, an electrode pattern formed on the test piece is used as an antenna, and as a result radio waves can be emitted efficiently even when the apparatus is held in the hand, so there is broad applicability to biological sample measurement apparatus that are used by inserting a test piece into a case, such as a blood glucose measurement device, for example.

The invention claimed is:

1. A biological sample measurement apparatus, comprising:
    a test piece for measuring a biological sample having a measurement electrode for electrochemically measuring the biological sample that has been placed in the form of a spot in a specific location;
    a test piece insertion unit for inserting, holding, and electrically connecting the test piece;
    a measurement circuit for electrochemically measuring a biological sample that has been placed in the form of a spot on the test piece;
    a communication circuit for transmitting the result measured with the measurement circuit by wireless communication by using the measurement electrode of the test piece connected via the test piece insertion unit as a communications antenna; and
    a switch that is connected to the test piece insertion unit, for switching between the measurement circuit and the communication circuit.

2. The biological sample measurement apparatus according to claim 1,
    further comprising an insertion/removal detection circuit for detecting that the test piece has been inserted into the test piece insertion unit.

3. The biological sample measurement apparatus according to claim 2,
    further comprising an auxiliary antenna connected to the communication circuit; and
    a communication controller for controlling communication in the communication circuit,
    wherein the communication controller instructs the communication circuit to retransmit via the auxiliary antenna if communication has not been completed upon detection by the insertion/removal detection circuit that no test piece has been mounted.

4. The biological sample measurement apparatus according to claim 2,
    further comprising a communication controller for controlling communication in the communication circuit,
    wherein the communication controller instructs the communication circuit to retransmit upon detection of the insertion of the next test piece if communication has not been completed upon detection by the insertion/removal detection circuit that no test piece has been mounted.

5. The biological sample measurement apparatus according to claim claim 1,
    further comprising a display device for displaying the result of measurement by the measurement circuit; and
    a display controller for controlling the display of the display device,
    wherein the display controller controls the display device so that the result of measurement is not displayed until the transmission of the measurement result by the communication circuit is complete.

6. The biological sample measurement apparatus according to claim claim 1,
    further comprising a display device for displaying the result of measurement by the measurement circuit; and
    a display controller for controlling the display of the display device,
    wherein the display controller controls the display device so that the fact that communication is in progress is displayed until transmission of the result of measurement by the communication circuit is complete.

7. A biological sample measurement apparatus, comprising:
    a test piece for measuring a biological sample having a measurement electrode for electrochemically measuring the biological sample that has been placed in the form of a spot in a specific location and an antenna electrode that functions as a communications antenna;
    a test piece insertion unit for inserting, holding, and electrically connecting the test piece;
    a measurement circuit for electrochemically measuring a biological sample that has been placed in the form of a spot on the test piece;
    a communication circuit for transmitting the result measured with the measurement circuit by wireless communication by using the antenna electrode of the test piece connected via the test piece insertion unit; and an antenna pattern disposed between the communication circuit and an electrode within the test piece insertion unit to which the antenna electrode of the test piece is connected.

8. The biological sample measurement apparatus according to claim 7,
further comprising an insertion/removal detection circuit for detecting that the test piece has been inserted into the test piece insertion unit.

9. The biological sample measurement apparatus according to claim 8,
further comprising an auxiliary antenna connected to the communication circuit; and
a communication controller for controlling communication in the communication circuit,
wherein the communication controller instructs the communication circuit to retransmit via the auxiliary antenna if communication has not been completed upon detection by the insertion/removal detection circuit that no test piece has been mounted.

10. The biological sample measurement apparatus according to claim 8,
further comprising a communication controller for controlling communication in the communication circuit,
wherein the communication controller instructs the communication circuit to retransmit upon detection of the insertion of the next test piece if communication has not been completed upon detection by the insertion/removal detection circuit that no test piece has been mounted.

11. The biological sample measurement apparatus according to claim 7,
further comprising a display device for displaying the result of measurement by the measurement circuit; and
a display controller for controlling the display of the display device,
wherein the display controller controls the display device so that the result of measurement is not displayed until the transmission of the measurement result by the communication circuit is complete.

12. The biological sample measurement apparatus according to claim 7,
further comprising a display device for displaying the result of measurement by the measurement circuit; and
a display controller for controlling the display of the display device,
wherein the display controller controls the display device so that the fact that communication is in progress is displayed until transmission of the result of measurement by the communication circuit is complete.

13. A biological sample measurement apparatus, comprising:
a test piece for measuring a biological sample having a measurement electrode for electrochemically measuring the biological sample that has been placed in the form of a spot in a specific location and an antenna electrode that functions as a communications antenna;
a test piece insertion unit for inserting, holding, and electrically connecting the test piece;
a measurement circuit for electrochemically measuring a biological sample that has been placed in the form of a spot on the test piece; and
a communication circuit for transmitting the result measured with the measurement circuit by wireless communication by using the antenna electrode of the test piece connected via the test piece insertion unit;
an insertion/removal detection circuit for detecting that the test piece has been inserted into the test piece insertion unit;
an auxiliary antenna connected to the communication circuit; and
a communication controller for controlling communication in the communication circuit,
wherein the communication controller instructs the communication circuit to retransmit via the auxiliary antenna if communication has not been completed upon detection by the insertion/removal detection circuit that no test piece has been mounted.

14. The biological sample measurement apparatus according to claim 13,
further comprising a display device for displaying the result of measurement by the measurement circuit; and
a display controller for controlling the display of the display device,
wherein the display controller controls the display device so that the result of measurement is not displayed until the transmission of the measurement result by the communication circuit is complete.

15. The biological sample measurement apparatus according to claim 13,
further comprising a display device for displaying the result of measurement by the measurement circuit; and
a display controller for controlling the display of the display device,
wherein the display controller controls the display device so that the fact that communication is in progress is displayed until transmission of the result of measurement by the communication circuit is complete.

16. A biological sample measurement apparatus, comprising:
a test piece for measuring a biological sample having a measurement electrode for electrochemically measuring the biological sample that has been placed in the form of a spot in a specific location and an antenna electrode that functions as a communications antenna;
a test piece insertion unit for inserting, holding, and electrically connecting the test piece;
a measurement circuit for electrochemically measuring a biological sample that has been placed in the form of a spot on the test piece; and
a communication circuit for transmitting the result measured with the measurement circuit by wireless communication by using the antenna electrode of the test piece connected via the test piece insertion unit;
an insertion/removal detection circuit for detecting that the test piece has been inserted into the test piece insertion unit;
a communication controller for controlling communication in the communication circuit,
wherein the communication controller instructs the communication circuit to retransmit upon detection of the insertion of the next test piece if communication has not been completed upon detection by the insertion/removal detection circuit that no test piece has been mounted.

* * * * *